United States Patent
Wagner

(10) Patent No.: US 10,188,672 B2
(45) Date of Patent: Jan. 29, 2019

(54) COMPOSITIONS AND METHODS FOR TISSUE REGENERATION

(71) Applicant: ORBIS HEALTH SOLUTIONS, LLC, Greenville, SC (US)

(72) Inventor: Thomas E. Wagner, Greenville, SC (US)

(73) Assignee: Orbis Health Solutions LLC, Greenville, SC (US)

(*) Notice: Subject to any disclaimer, the term of this patent is extended or adjusted under 35 U.S.C. 154(b) by 0 days.

(21) Appl. No.: 14/103,116

(22) Filed: Dec. 11, 2013

(65) Prior Publication Data

US 2014/0161912 A1     Jun. 12, 2014

Related U.S. Application Data

(60) Provisional application No. 61/736,257, filed on Dec. 12, 2012, provisional application No. 61/786,380, filed on Mar. 15, 2013.

(51) Int. Cl.

| | |
|---|---|
| A61K 36/00 | (2006.01) |
| A61K 31/695 | (2006.01) |
| A61K 36/185 | (2006.01) |
| A61K 36/63 | (2006.01) |
| A61K 36/736 | (2006.01) |
| A61K 36/886 | (2006.01) |
| A61K 35/644 | (2015.01) |
| A61K 9/00 | (2006.01) |
| A61K 8/58 | (2006.01) |
| A61Q 19/00 | (2006.01) |
| A61K 8/92 | (2006.01) |
| A61K 36/88 | (2006.01) |
| A61K 45/06 | (2006.01) |
| A61K 9/06 | (2006.01) |

(52) U.S. Cl.
CPC ............ *A61K 31/695* (2013.01); *A61K 8/585* (2013.01); *A61K 8/922* (2013.01); *A61K 9/0017* (2013.01); *A61K 35/644* (2013.01); *A61K 36/185* (2013.01); *A61K 36/63* (2013.01); *A61K 36/736* (2013.01); *A61K 36/88* (2013.01); *A61K 36/886* (2013.01); *A61K 45/06* (2013.01); *A61Q 19/00* (2013.01); *A61K 9/06* (2013.01)

(58) Field of Classification Search
CPC ...................................... A61K 36/00
USPC ........................................ 424/725
See application file for complete search history.

(56) References Cited

U.S. PATENT DOCUMENTS

| | | | |
|---|---|---|---|
| 4,454,110 A | 6/1984 | Caslaysky et al. | |
| 4,563,351 A | 1/1986 | Caslavsky et al. | |
| 6,846,499 B2 * | 1/2005 | El Mogy | A61K 8/922 424/725 |
| 2001/0006623 A1 | 7/2001 | Warford, III et al. | |
| 2002/0064541 A1 | 5/2002 | Lapidot et al. | |
| 2005/0059151 A1 | 3/2005 | Bosch et al. | |
| 2006/0104986 A1 | 5/2006 | Duke et al. | |
| 2008/0254537 A1 | 10/2008 | Boynton et al. | |
| 2009/0232902 A1 * | 9/2009 | Liu | A61L 15/18 424/601 |
| 2012/0070376 A1 | 3/2012 | Ostroff et al. | |

FOREIGN PATENT DOCUMENTS

| | | |
|---|---|---|
| EP | 2096151 A1 | 2/2009 |
| JP | 05331044 * | 12/1993 |
| JP | H08-143447 A | 5/1996 |
| JP | 408143447 A * | 6/1996 |
| JP | 2003-089629 A | 3/2003 |
| WO | WO 99/30629 A1 | 6/1999 |
| WO | WO 02/39951 A2 | 5/2002 |
| WO | WO 2005/009604 A1 | 2/2005 |
| WO | WO 2012/082450 A2 | 6/2012 |

OTHER PUBLICATIONS

Pub Chem, 49 pages, 2015.*
Kotera et al., "Comparative Analysis of Necrotic and Apoptotic Tumor Cells As a Source of Antigen(s) in Dendritic Cell-based Immunization," Cancer Research, Nov. 15, 2001, 61:8105-8109.
Euro Stem Cell, "Regeneration: what does it mean and how does it work?", 2016, 3 pages.
Colino et al,. "Dendritic Cells Pulsed with Intact *Streptococcus pneumonia* Elicit both Protein- and Polysaccharide-specific Immunoglobulin Isotype Responses In Vivo though Distinct Mechanisms," J. Exp. Med., Jan. 7, 2002, 195(1):1-13.
Day et al., Eds., Cryopreservation and Freeze-Drying Protocols, 2007, p. 10, Table 4.
Foged et al., "Particle size and surface charge affect particle uptake by human dendritic cells in an in vitro model," International Journal of Pharmaceutics, 2005, 298:315-322.
Strome et al., "Strategies for Antigen Loading of Dendritic Cells to Enhance the Antitumor Immune Response," Cancer Res., 2002, 62:1884-1889.
Keeler et al., "The Metabolism of Silicon in the Rat and its Relation to the Formation of Artificial Siliceous Calculi," The Journal of Experimental Medicine, 1959, 109(6):601-614.
Ma et al., Handbook of Skin Cosmetic and Cosmetic Preparations, Mar. 2004, p. 89, with English translation.

* cited by examiner

*Primary Examiner* — Michael V Meller
(74) *Attorney, Agent, or Firm* — Foley & Lardner LLP

(57) ABSTRACT

Methods and compositions using an orthosilicate for tissue regeneration, such as to treat a disease or condition, are described, including on the skin. Also described are methods for making such compositions.

11 Claims, 17 Drawing Sheets

FIGURE 9A
FIGURE 9B
Original Bite
5 Days Post Trauma

FIGURE 12A
FIGURE 12B
FIGURE 12C
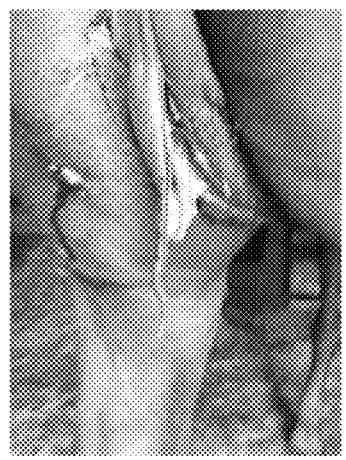
Original Trauma
10 Days Post Trauma
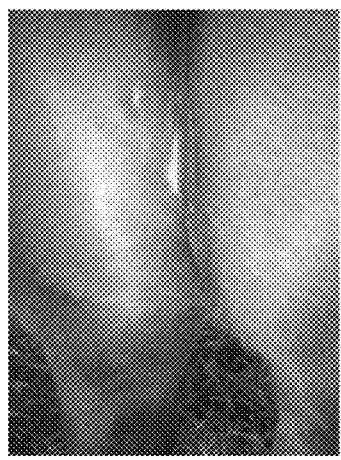
21 Days Post Trauma

COMPOSITIONS AND METHODS FOR TISSUE REGENERATION

CROSS-REFERENCE TO RELATED APPLICATIONS

This application claims priority to U.S. provisional patent application Nos. 61/736,257, filed on Dec. 12, 2012, and 61/786,380, filed on Mar. 15, 2013. The contents of the prior applications are incorporated herein by reference in their entireties.

FIELD OF THE INVENTION

Described herein are methods and compositions using an orthosilicate for providing tissue regeneration, such as to treat a disease or condition, including on the skin. Also described are methods for making such compositions.

BACKGROUND

Damage to skin, underlying muscle and other surrounding tissue can occur as the result of a number of diseases and conditions. Such damage can be long-lasting and result in physical damage to these tissues.

For example, acne develops because pores in the skin are clogged with oil from hair follicles, resulting in a build up of matter such as bacteria and cells. If left untreated, long-lasting acne can result in scarring and disfigurement of a person's skin, such as on the person's face.

Additionally, different types of skin cancer, resulting from the uncontrolled growth of abnormal skin cells, cause physical damage to the skin and can be deadly if left untreated. For example, roughly 120,000 people in the United States are diagnosed with melanoma annually and roughly 8,790 people in the United States die from the disease annually. Melanoma develops when melanocytes produce malignant tumors as a result of overexposure to ultraviolet radiation, either from the sun or artificial lighting. Malignant tumors generally show up as large, colorful (generally dark), asymmetrical spots on the skin, thus causing disfigurement of the skin.

Likewise, basal cell carcinoma, another type of skin cancer, is evident from abnormal spots on the skin, including on the scalp of the head, which can present a variety of symptoms that affect the physical appearance of skin and cause damage to the skin and underlying tissues.

Furthermore, demodectic mange is a dermatological condition in canines caused by mites, resulting from an inability of a canine's immune system to control the mites. Demodectic mange causes hair loss and can lead to a breakdown of skin, resulting in itching, scabbing, sores and other disfigurement of the skin and/or underlying tissues.

A puncture wound results in tissue damage, both to the skin and underlying tissues. In some cases, excessive bleeding and infection can occur as the result of a puncture wound. Other diseases and conditions relate to tissue damage, including hair loss.

Accordingly, the foregoing examples represent diseases and conditions that involve tissue damage, either to the skin, muscle or related tissues. The presently claimed invention addresses such diseases and conditions, as described herein.

SUMMARY OF THE INVENTION

One embodiment of the present invention is directed to a composition comprising an orthosilicate represented by $Si(OR)_4$, wherein R is a $C_1$-$C_{12}$ alkyl and wherein the orthosilicate is present in a concentration from about 10% to about 40%. In some embodiments, R is a $C_2$ alkyl. In some embodiments, the composition further comprises an oil. In some embodiments, the oil is selected from the group consisting of aloe vera oil, chamomile oil, geranium oil, jojoba oil, juniper oil, lavender oil, palm oil, sunflower oil and vanilla oil, almond oil, sweet almond oil, peanut oil, cashew oil, hazelnut oil, macadamia oil, mongongo nut oil, pecan oil, pine nut oil, pistachio oil, walnut oil, avocado oil, cocoa butter oil, coconut oil, corn oil, grapeseed oil, olive oil, sesame oil, shea butter oil and soybean oil. In some embodiments, the oil is selected from the group consisting of jojoba oil, almond oil and olive oil. In some embodiments, the composition further comprises one or more components selected from the group consisting of an excipient, stabilizer, moisturizer, thickening agent, emulsifier, emollient, lubricant, surfactant, deodorizing agent, viscosity controlling agent, solvent, softening agent, alkalizing agent, vitamin, opacifying agent, solubilizer, plant extract, water, chelating agent, humectant, thickener, cryoprotectant, biocide, nebulizer, anti-oxidant, lipid, peptide, protein, amino acid, anti-aging agent, anti-wrinkle agent, fragrance, essential oil, and preservative.

Another embodiment of the present invention is directed to a composition comprising essentially of an orthosilicate represented by $Si(OR)_4$ and an oil, wherein R is a $C_1$-$C_{12}$ alkyl and wherein the orthosilicate is present in a concentration from about 10% to about 40%. In some embodiments, R is a $C_2$ alkyl. In some embodiments, the oil is selected from the group consisting of jojoba oil, almond oil and olive oil.

In yet another embodiment of the present invention is directed to a composition comprising essentially of an orthosilicate represented by $Si(OR)_4$, sweet almond oil, cocoa butter and beeswax, wherein R is a $C_1$-$C_{12}$ alkyl and wherein the orthosilicate is present in a concentration from about 10% to about 40%. In some embodiments, R is a $C_2$ alkyl. In some embodiments, the orthosilicate is present in a concentration of 20%.

Also described in the present invention is a method for treating a condition or disease requiring tissue regeneration, comprising administering to a subject in need thereof a composition comprising an orthosilicate represented by $Si(OR)_4$, wherein R is a $C_1$-$C_{12}$ alkyl and wherein the orthosilicate is present in a concentration from 10% to 40%, and a composition for treating the same. In some embodiments, R is a $C_2$ alkyl. In some embodiments, the composition further comprises an oil. In some embodiments, the oil is selected from the group consisting of aloe vera oil, chamomile oil, geranium oil, jojoba oil, juniper oil, lavender oil, palm oil, sunflower oil and vanilla oil, almond oil, sweet almond oil, peanut oil, cashew oil, hazelnut oil, macadamia oil, mongongo nut oil, pecan oil, pine nut oil, pistachio oil, walnut oil, avocado oil, cocoa butter oil, coconut oil, corn oil, grapeseed oil, olive oil, sesame oil, shea butter oil and soybean oil. In some embodiments, the oil is selected from the group consisting of jojoba oil, almond oil and olive oil. In some embodiments, the condition or disease is selected from the group consisting of acne, a puncture wound and surface lesion due to melanoma or basal cell carcinoma. In some embodiments, the composition further comprises a component selected from the group consisting of an excipient, stabilizer, moisturizer, thickening agent, emulsifier, emollient, lubricant, surfactant, deodorizing agent, viscosity controlling agent, solvent, softening agent, alkalizing agent, vitamin, opacifying agent, solubilizer, plant extract, water, chelating agent, humectant, thickener, cryoprotectant, biocide, nebulizer, anti-oxidant, lipid, peptide, protein, amino acid, anti-aging agent, anti-wrinkle agent, fragrance, essential oil, and preservative.

The present invention also describes a method of preparing a composition, comprising physically mixing an orthosilicate represented by $Si(OR)_4$ and an oil, wherein R is a $C_1$-$C_{12}$ alkyl and wherein the orthosilicate is present in a concentration from about 10% to about 40%. In some embodiments, R is a $C_2$ alkyl. In some embodiments, the oil is selected from the group consisting of aloe vera oil, chamomile oil, geranium oil, jojoba oil, juniper oil, lavender oil, palm oil, sunflower oil and vanilla oil, almond oil, sweet almond oil, peanut oil, cashew oil, hazelnut oil, macadamia oil, mongongo nut oil, pecan oil, pine nut oil, pistachio oil, walnut oil, avocado oil, cocoa butter oil, coconut oil, corn oil, grapeseed oil, olive oil, sesame oil, shea butter oil and soybean oil. In some embodiments, the oil is selected from the group consisting of jojoba oil, almond oil and olive oil. In some embodiments, the method further comprises mixing a component selected from the group consisting of an excipient, stabilizer, moisturizer, thickening agent, emulsifier, emollient, lubricant, surfactant, deodorizing agent, viscosity controlling agent, solvent, softening agent, alkalizing agent, vitamin, opacifying agent, solubilizer, plant extract, water, chelating agent, humectant, thickener, cryoprotectant, biocide, nebulizer, anti-oxidant, lipid, peptide, protein, amino acid, anti-aging agent, anti-wrinkle agent, fragrance, essential oil, and preservative.

In another aspect, the present invention relates to use of the compositions encompassed by the invention in treating a condition or disease requiring tissue regeneration. The condition or disease includes, but is not limited to, skin damages, acne, different types of skin cancers, puncture wound, or other dermatological conditions.

BRIEF DESCRIPTION OF THE DRAWINGS

FIGS. 9A-9B depict an infected bite wound in an adult Australian Shepherd before treatment with a composition comprising orthosilicate (FIG. 9A) and after 5 days of treatment with the composition (FIG. 9B).

FIGS. 12A-12C depict the wound before the treatment with a composition comprising orthosilicate (FIG. 12A), after 10 days of treatment with the composition (FIG. 12B), and after 21 days of treatment with the composition (FIG. 12C).

DETAILED DESCRIPTION

Figure 1A:
FIGS. 1A-1D depict an individual with acne before treatment with a composition comprising orthosilicate (FIGS. 1A-1B), after 1 week of treatment with the composition (FIG. 1C) and 4 weeks after treatment with the composition (FIG. 1D).

Described herein are methods and compositions using an orthosilicate for treating various diseases and conditions by regenerating tissue, including on the skin. Also described herein are methods for making such compositions.

In this specification, reference is made herein to various methodologies known to those of ordinary skill in the art. Publications and other materials setting forth such known methodologies to which reference is made are incorporated herein by reference in their entirety as though set forth in full.

I. DEFINITIONS

As used herein, the singular forms "a," "an," and "the" designate both the singular and the plural, unless expressly stated to designate the singular only. Likewise, singular forms of terms designate both the singular and plural, unless expressly stated to designate the singular only. For example, "composition" means "composition" or "compositions."

The term "about" in connection with numerical values and ranges means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used.

As used herein "subject" or "patient" denotes any animal in need of treatment with a composition. For example, a subject may be suffering from or at risk of developing a condition that can be treated or prevented with a composition comprising an orthosilicate. As used herein "subject" or "patient" includes humans.

As used herein, the phrases "therapeutically effective amount" and "therapeutic level" mean that dosage in a subject, respectively, that provides the specific response for which the composition is administered in a subject in need of such treatment. For convenience only, exemplary dosages, delivery amounts, therapeutically effective amounts and therapeutic levels are provided below with reference to adult human subject. Those skilled in the art can adjust such amounts in accordance with standard practices as needed to treat a specific subject and/or condition/disease.

As used herein, the phrases "tissue regeneration" or "regenerate a tissue" or related phrases including "tissue" and "regenerate" or "regeneration," mean that tissue that has been damaged is being healed or has been healed. In some embodiments, these phrases also mean that the underlying disease or condition is being treated or has been treated.

II. ORTHOSILICATES

Orthosilicates useful in the compositions and methods described herein are represented by the following formula: $Si(OR)_4$, wherein R is a $C_1$-$C_{12}$ alkyl.

In some embodiments, compositions and methods include an orthosilicate comprising a methyl group. In other embodiments, the compositions and methods include an orthosilicate comprising an ethyl group. In other embodiments, the compositions and methods include an orthosilicate comprising a propyl group. In other embodiments, the compositions and methods include an orthosilicate comprising an butyl group. In other embodiments, the compositions and methods include an orthosilicate comprising a pentyl group. In other embodiments, the compositions and methods include an orthosilicate comprising a hexyl group. In other embodiments, the compositions and methods include an orthosilicate comprising an heptyl group. In other embodiments, the compositions and methods include an orthosilicate comprising an octyl group. In other embodiments, the compositions and methods include an orthosilicate comprising a nonyl group. In other embodiments, the compositions and methods include an orthosilicate comprising a decyl group. In other embodiments, the compositions and methods include an orthosilicate comprising an undecyl group. In other embodiments, the compositions and methods include an orthosilicate comprising a dodecyl group.

In some embodiments, compositions and methods described herein include a tetraethyl orthosilicate.

In some embodiments, the orthosilicates are present in the compositions in a range from about 10% to about 60%, including from about 10% to about 55%, from about 10% to about 50%, from about 10% to about 45%, from about 10% to about 40%, from about 10% to about 35%, from about 10% to about 30%, from about 10% to about 25%, from about 10% to about 20%, from about 10% to about 15%, from about 15% to about 60%, from about 15% to about 55%, from about 15% to about 50%, from about 15% to about 45%, from about 15% to about 40%, from about 15% to about 35%, from about 15% to about 30%, from about 15% to about 25%, from about 15% to about 20%, from about 20% to about 60%, from about 20% to about 55%, from about 20% to about 50%, from about 20% to about 45%, from about 20% to about 40%, from about 20% to about 35%, from about 20% to about 30%, from about 20% to about 25%, from about 25% to about 60%, from about 25% to about 55%, from about 25% to about 50%, from about 25% to about 45%, from about 25% to about 40%, from about 25% to about 35%, from about 25% to about 30%, from about 30% to about 60%, from about 30% to about 55%, from about 30% to about 50%, from about 30% to about 45%, from about 30% to about 40%, from about 30% to about 35%, from about 35% to about 60%, from about 35% to about 55%, from about 35% to about 50%, from about 35% to about 45%, from about 35% to about 40%, from about 40% to about 60%, from about 40% to about 55%, from about 40% to about 50%, from about 40% to about 45%, from about 45% to about 60%, from about 45% to about 55%, from about 45% to about 50%, from about 50% to about 60%, from about 50% to about 55%, from about 55% to about 60%, such as about 10%, about 15%, about 20%, about 25%, about 30%, about 35%, about 40%, about 45%, about 50%, about 55% and about 60%.

In some embodiments, the orthosilicates are present in the composition in a range from 10% to 60%, including from 10% to 55%, from 10% to 50%, from 10% to 45%, from 10% to 40%, from 10% to 35%, from 10% to 30%, from 10% to 25%, from 10% to 20%, from 10% to 15%, from 15% to 60%, from 15% to 55%, from 15% to 50%, from 15% to 45%, from 15% to 40%, from 15% to 35%, from 15% to 30%, from 15% to 25%, from 15% to 20%, from 20% to 60%, from 20% to 55%, from 20% to 50%, from 20% to 45%, from 20% to 40%, from 20% to 35%, from 20% to 30%, from 20% to 25%, from 25% to 60%, from 25% to 55%, from 25% to 50%, from 25% to 45%, from 25% to 40%, from 25% to 35%, from 25% to 30%, from 30% to 60%, from 30% to 55%, from 30% to 50%, from 30% to 45%, from 30% to 40%, from 30% to 35%, from 35% to 60%, from 35% to 55%, from 35% to 50%, from 35% to 45%, from 35% to 40%, from 40% to 60%, from 40% to 55%, from 40% to 50%, from 40% to 45%, from 45% to 60%, from 45% to 55%, from 45% to 50%, from 50% to 60%, from 50% to 55%, from 55% to 60%, such as 10%, 15%, 20%, 25%, 30%, 35%, 40%, 45%, 50%, 55% and 60%.

In some embodiments, the orthosilicates present in compositions described herein do not polymerize after contact with an aqueous environment, such as an in vivo environment. Without being bound by theory, it is believed that the lack of such polymerization allows the orthosilicates to effectively treat a disease or condition by regenerating tissue.

Also without being bound by theory, it is believed that the compositions described herein regenerate tissue by activating the innate immune system, thus inducing the body to produce a response to tissue damage and assist in the regeneration of tissue.

In this regard, macrophages, the principal action cell of the innate immune system, targets cells that display markers in the form of pathogen associated molecular profiles (pamp's) or damage associated molecular profiles (damp's) on their membrane surface. The macrophages will phagocytize cells displaying such markers. Such phagocytic activity is also associated with the release of chemokines from the activated macrophages, which further attracts more monocytes that in turn differentiate into more macrophages, flooding the sites where cells displaying pamp's or damp's are present. Not only will this flood of macrophages clear any nearby pathogens and/or diseased or dying cells, but also, once any such cells are destroyed, the entire gene expression profile of these macrophages changes so that the macrophages become engaged in tissue remodeling and repair.

Thus, it is believed that orthosilicates interact with the external membranes of damaged or dying cells to decorate these cells such that they now display dramatically "super" damp's that maximally activate macrophages and maximally trigger the above-stated response. It is also believed that even perfectly normal tissue (e.g., normal skin) contain dying cells, so orthosilicates interact with triggering the repair/remodeling response to produce tissue regeneration in many applications (e.g., for cosmetic applications).

In some embodiments, the compositions described herein include water. In other embodiments, the compositions described herein to not include water.

III. OILS

Oils suitable for use in the compositions and methods described herein include oils derived from a plant, flower, nut, fruit, seed and vegetable.

In some embodiments, the compositions include one or more of the following oils derived from a plant or flower: aloe vera oil, chamomile oil, geranium oil, jojoba oil, juniper oil, lavender oil, palm oil, sunflower oil and vanilla oil.

In other embodiments, the compositions include one or more of the following oils derived from a nut: almond oil, sweet almond oil, peanut oil, cashew oil, hazelnut oil, macadamia oil, mongongo nut oil, pecan oil, pine nut oil, pistachio oil and walnut oil.

In other embodiments, the compositions include one or more oils derived from a fruit, seed or vegetable: avocado oil, cocoa butter oil, coconut oil, corn oil, grapeseed oil, olive oil, sesame oil, shea butter oil and soybean oil.

In some embodiments, an oil suitable for the compositions described herein is a hydrophobic medium. In some embodiments, the oil is a long chain alcohol or acid.

The oils can be included in the compositions in an amount of from about 10% to about 90%, including about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, about 85% to about 90%, such as about 10%, about 15%, about 20%, about 25%, about 30%, about 35%, about 40%, about 45%, about 50%, about 55%, about 60%, about 65%, about 70%, about 75%, about 80%, about 85% and about 90%.

The oils can be included in the compositions in an amount of from 10% to 90%, including 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 90%, 15% to 85%, 15% to 80%, 15% to 75%, 15% to 70%, 15% to 65%, 15% to 60%, 15% to 55%, 15% to 50%, 15% to 45%, 15% to 40%, 15% to 35%, 15% to 30%, 15% to 25%, 15% to 20%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 90%, 40% to 85%, 40% to 80%, 40% to 75%, 40% to 70%, 40% to 65%, 40% to 60%, 40% to 55%, 40% to 50%, 40% to 45%, 45% to 90%, 45% to 85%, 45% to 80%, 45% to 75%, 45% to 70%, 45% to 65%, 45% to 60%, 45% to 55%, 45% to 50%, 50% to 90%, 50% to 85%, 50% to 80%, 50% to 75%, 50% to 70%, 50% to 65%, 50% to 60%, 50% to 55%, 55% to 90%, 55% to 85%, 55% to 80%, 55% to 75%, 55% to 70%, 55% to 65%, 55% to 60%, 60% to 90%, 60% to 85%, 60% to 80%, 60% to 75%, 60% to 70%, 60% to 65%, 65% to 90%, 65% to 85%, 65% to 80%, 65% to 70%, 70% to 90%, 70% to 85%, 70% to 80%, 70% to 75%, 75% to 90%, 75% to 85%, 75% to 80%, 80% to 90%, 80% to 85%, 85% to 90%, such as 10%, 15%, 20%, 25%, 30%, 35%, 40%, 45%, 50%, 55%, 60%, 65%, 70%, 75%, 80%, 85% and 90%.

Without being bound by theory, it is believed that the orthosilicates, when administered to a subject in the presence of oil in the compositions described herein, become protected inside a micelle formed by the oil in the presence of surfactants, either naturally within the tissue or added in the composition. In some embodiments, such protection leads to the ability of the orthosilicates to regenerate tissue in vivo.

III. COMPOSITIONS

Described herein are compositions comprising one or more orthosilicates and oils, as described herein. The compositions can include one or more orthosilicates and oils in the same or different compositions for administration to a subject. In some preferred embodiments, one or more orthosilicates and one or more oils are contained in the same composition. In other embodiments, one or more orthosilicates and one or more oils are separately applied.

In some embodiments, the compositions described herein include one or more additional components, such as a diluent, penetration enhancer, excipient, stabilizer, moisturizer, thickening agent, emulsifier, emollient, lubricant, surfactant, deodorizing agent, viscosity controlling agent (such as a viscosity increasing agent and a viscosity decreasing agent), solvent, softening agent, alkalizing agent (including to adjust pH), vitamin, opacifying agent, solubilizer, plant extract, water (including purified water), chelating agent, humectant, thickener, cryoprotectant, biocide, adjuvant, nebulizer, anti-oxidant, lipid, peptide, protein, amino acid, anti-aging agent, anti-wrinkle agent, fragrance, essential oil, preservative, and combinations thereof.

In some embodiments, the compositions described herein include one or more additional components, such as Isopropyl Palmitate, Lecithin, C12-15 Alkyl Benzoate, Cetyl Alcohol, Cetearyl Alcohol, Ethylhexylglycerin, Glycerin USP, Glyceryl Stearate, Hydroxyethyl Acrylate/Sodium, Acryloyldimethyl Taurate Copolymer, Oleic Acid, PEG 100 Stearate, Phenoxyethanol, Polymethylsiloxane, Purified Water, Stearic Acid, Trolamine NF, Vitamin E, Vitamin E Acetate, Ethylhexyl Stearate, Glycerol Stearate, PEG 100 Stearate, Polysorbate-60, Aloe, Leaf Juice, EDTA, Sorbitol, Cyclomethicone, Isothiazolinone, Propylene Glycol, Ceteareth 20, Dimethicone, Octyldodecanol, Phenoxyethanol, Bees wax and combinations thereof.

The one or more additional components can be included in the composition in an amount from about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 80%, about 40% to about 75%, about 40% to about 70%, about 40% to about 65%, about 40% to about 60%, about 40% to about 55%, about 40% to about 50%, about 40% to about 45%, about 45% to about 80%, about 45% to about 75%, about 45% to about 70%, about 45% to about 65%, about 45% to about 60%, about 45% to about 55%, about 45% to about 50%, about 50% to about 80%, about 50% to about 75%, about 50% to about 70%, about 50% to about 65%, about 50% to about 60%, about 50% to about 65%, about 50% to about 60%, about 50% to about 55%, about 55% to about 80%, about 55% to about 75%, about 55% to about 70%, about 55% to about 65%, about 55% to about 60%, about 60% to about 80%, about 60% to about 75%, about 60% to about 70%, about 60% to about 65%, about 65% to about 80%, about 65% to about 75%, about 65% to about 70%, about 70% to about 80%, about 70% to about 75%, about 75% to about 80%, such as about 10%, about 15%, about 20%, about 25%, about 30%, about 35%, about 40%, about 45%, about 50%, about 55%, about 60%, about 65%, about 70%, about 75% and about 80%.

The one or more additional components can be included in the compositions in an amount of from 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 80%, 15% to 75%, 15% to 70%, 15% to 65%, 15% to 60%, 15% to 55%, 15% to 50%, 15% to 45%, 15% to 40%, 15% to 35%, 15% to 30%, 15% to 25%, 15% to 20%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 80%, 30% to 75%, 30% to 70%, 30% to 65%, 30% to 60%, 30% to 55%, 30% to 50%, 30% to 45%, 30% to 40%, 30% to 35%, 35% to 80%, 35% to 75%, 35% to 70%, 35% to 65%, 35% to 60%, 35% to 55%, 35% to 50%, 35% to 45%, 35% to 40%, 40% to 80%, 40% to 75%, 40% to 70%, 40% to 65%, 40% to 60%, 40% to 55%, 40% to 50%, 40% to 45%, 45% to 80%, 45% to 75%, 45% to 70%, 45% to 65%, 45% to 60%, 45% to 55%, 45% to 50%, 50% to 80%, 50% to 75%, 50% to 70%, 50% to 65%, 50% to 60%, 50% to 65%, 50% to 60%, 50% to 55%, 55% to 80%, 55% to 75%, 55% to 70%, 55% to 65%, 55% to 60%, 60% to 80%, 60% to 75%, 60% to 70%, 60% to 65%, 65% to 80%, 65% to 75%, 65% to 70%, 70% to 80%, 70% to 75%, 75% to 80%, such as 10%, 15%, 20%, 25%, 30%, 35%, 40%, 45%, 50%, 55%, 60%, 65%, 70%, 75% and 80%.

IV. METHODS OF MAKING

The compositions described herein can be presented in different forms. In one embodiment, the compositions are presented for topical application, such as a cosmetic. In another embodiment, the compositions are presented as a cream. In another embodiment, the compositions are presented as a gel. In another embodiment, the compositions are presented as a lotion. In another embodiment, the compositions are presented as an ointment. In another embodiment, the compositions are presented as a paste. In another embodiment, the compositions are presented as a patch. In another embodiment, the compositions are presented as soaps.

In one embodiment, the compositions are prepared by combining one or more orthosilicates with one or more oils and physically mixing the orthosilicate(s) and oil(s). In another embodiment, the compositions are prepared by combining one or more orthosilicates with one or more oils and one or more additional components, including optionally water, and physically mixing the orthosilicate(s), oil(s), additional component(s) and optionally water.

V. METHODS OF USE

The compositions as described herein are useful for treating a variety of diseases and conditions. As described herein, the compositions are useful for remodeling tissue, including the skin.

In some embodiments, the compositions are useful as topical applications, such as for cosmetic applications. In some embodiments, the compositions are useful as pharmaceutical applications.

As described herein, the compositions are useful for treating tissue damage. In some embodiments, the compositions are useful for treating a physical wound, scarring and a dermatological condition, such as acne, demodectic mange and surface lesion from skin cancer, such as melanoma and basal cell carcinoma.

In some embodiments, the compositions are applied by topical administration onto a body surface, including the skin, nail, or mucosa. In some embodiments, the compositions are topically applied by smearing or rubbing the compositions onto the body surface. In some embodiments, the compositions are sprayed onto the body surface. In other some embodiments, the compositions are administered by droplet(s) from a dispenser, such as a syringe or eye dropper.

In some embodiments, the compositions described herein are applied once. In other embodiments, the compositions are applied multiple times, including applied multiple times a day for multiple days. For example, the compositions can be applied for 1, 2, 3, 4, 5, 6 or 7 or more days, such as for 1, 2, 3, 4, 5, 6, or 7 or more days.

In some embodiments, the compositions are applied multiple times for two weeks, such as 1, 2, 3, 4 or 5 times daily for up to two weeks. For example, the compositions can be applied 1, 2, 3, 4 or 5 times daily for up to one or two months. In other embodiments, the compositions are applied once or multiple times a day until the disease or condition being treated has been removed.

In some embodiments, the compositions described herein are administered with another active agent. In other embodiments, the compositions described herein are not administered with another active agent.

VI. EXAMPLES

The following examples are merely demonstrative and highlight the orthosilicate compounds and methods of making and methods of using such compounds, as described herein.

Example 1

A formulation (Formulation 1) containing orthosilicate was produced according to the methods described herein:
1. C12-15 Alkyl Benzoate
2. Caprylic/Capric Triglycerides
3. Cetyl Alcohol
4. Ethylhexylglycerin
5. Glycerin USP
6. Glyceryl Stearate
7. Hydroxyethyl Acrylate/Sodium
8. Acryloyldimethyl Taurate Copolymer
9. Oleic Acid
10. Olive Oil
11. PEG 100 Stearate
12. Phenoxyethanol
13. Polymethylsiloxane
14. Purified Water
15. Stearic Acid
16. Trolamine NF
17. Vitamin E Acetate
18. Tetraethyl Ortho silicate

Example 2

A formulation (Formulation 2) containing orthosilicate was produced according to the methods described herein:
1. Purified Water
2. Ethylhexyl Stearate
3. Cetearyl Alcohol
4. Polysorbate-60
5. Aloe
6. Leaf Juice
7. Vitamin E
8. EDTA
9. Sorbitol
10. Cyclomethicone
11. Isothiazolinone
12. Tetraethyl Orthosilicate

Example 3

A formulation (Formulation 3) containing orthosilicate was produced according to the methods described herein:
1. Purified Water
2. Isopropyl Palmitate
3. Caprylic/Capric Triglyceride
4. Propylene Glycol
5. Ceteareth 20
6. Cetearyl Alcohol
7. Glycerol Stearate
8. PEG 100 Stearate
9. Dimethicone
10. Octyldodecanol
11. Lecithin
12. Ethylhexylglycerin
13. Phenoxyethanol
14. Tetraethyl Orthosilicate

Example 4

A formulation (Formulation 4) containing orthosilicate was produced according to the methods described herein:
1. Jojoba oil
2. Tetraethyl Orthosilicate

Example 5

A formulation (Formulation 5) containing orthosilicate was produced according to the methods described herein:
1. Cocoa butter
2. Bees wax
3. Sweet Almond Oil
4. Orthosilicate

Example 6

A cosmetic formulation (Formulation 6) containing orthosilicate was produced according to the methods described herein. The ingredients and the amount for each ingredient in weight percentage are detailed in Table 1 below.

TABLE 1

Cosmetic Formulation

| Part | Ingredient | Amount (% w/w) |
|---|---|---|
| A | Distilled water | 40.73 |
| A | Sodium chloride | 1.00 |
| A | Phytic acid (e.g., Phytic Acid Extreme from Biosil Technologies, Inc.) | 0.25 |
| A | Citric acid | 0.01 |
| A | Aloe barbadensis leaf juice | 0.10 |
| A | Coco-Glucoside, Glyceryl Oleate (Lamesoft ® PO 65) | 2.00 |
| A | Cocamidopropyl PG-Dimonium Chloride Phosphate (Cola ® Lipid C) | 0.20 |
| B | Crodafos ™ CES (Blend of Cetearyl Alcohol, Dicetyl Phosphate, Ceteth-10 Phosphate) | 5.20 |
| B | C12-15 Alkyl Benzoate (Tegosoft ® TN 2) | 10.00 |
| B | Stearoxytrimethylsilane (SilCare Silicone ® 1M71) | 10.00 |
| B | Cetearyl Alcohol (Crodacol ™ 1618) | 0.10 |
| B | Glyceryl Oleate (Tegin ® O V) | 0.10 |
| B | Vinyl Dimethicone/Methicone Silsesquioxane crosspolymer (KSP-100) | 5.00 |
| C | Sodium hydroxide (10%) | 1.54 |
| C | IDEALIFT ™ (Blend of Butylene Glycol, Water, Sorbitan Laurate, Hydroxyethylcellulose and Acetyl Dipeptide-1 Cetyl Ester) | 2.00 |
| C | Arginine | 0.10 |
| C | Bisabolol | 0.05 |
| C | Fragrance extract blend (Sensique Ginger Euxyl 9010) | 0.20 |
| C | Phenoxyethanol, Ethylhexylglycerine | 1.00 |
| D | Tetraethoxysilane | 10.00 |
| D | Propylene Glycol | 1.00 |
| D | Glycerin | 2.00 |
| D | Dimethyl Isosorbide (Arlasolve ™ DMI) | 0.20 |
| D | Polysorbate 20 (Tween 20) | 4.00 |
| E | Sodium Citrate | 0.12 |
| E | MPC ™ - Milk Peptide Complex (whey protein) | 0.10 |
| E | Distilled water | 3.00 |

Formulation 6 was prepared as follows: the ingredients of Part A and Part B were combined and mixed separately, and each was heated with mixing to about 75° C. Then Part B was added to Part A with mixing, and mixing was continued for 15-20 minutes, until cooled to about 40° C. Part C was then added. Ingredients of Part D and Part E were premixed separately and each was added to the batch. The mixture was homogenized until uniform.

Example 7

Formula 5 from Example 5 was prepared as a cream in the following ratios: 20% tetraethyl orthosilicate; and equal amounts of cocoa butter, bees wax and sweet almond oil. To prepare the cream, the bees wax was melted and then combined with the sweet almond oil, cocoa butter and orthosilicate to produce a final concentration of 20% orthosilicate.

The prepared cream was applied to the face of a patient suffering from acne once every evening for 4 weeks.

Figure 1B:

FIGS. 1A-1B depicts the face of the patient before starting the 4-week period. FIG. 1B is a close-up of the patient's forehead, clearly depicting the presence of acne.

Figure 1C:

FIG. 1C depicts the forehead of the patient 1-week after initiating treatment with the cream. This figure demonstrates that the once-a-night application of the cream reduced the presence of the acne.

Figure 1D:

FIG. 1D depicts the face of the patient after completion of the 4-week period. This figure, combined with FIGS. 1A-1C, demonstrate that a cream composition containing orthosilicate significantly reduced the visible impact of acne on the patient's face.

Example 8

A composition containing 40% tetraethyl orthosilicate and 60% olive oil by volume was prepared by physical mixing. The composition was administered to a canine suffering from demodectic mange twice a day for 4 weeks.

Figure 2A:
FIGS. 2A-2D depict a canine with demodectic mange prior to treatment with a composition comprising orthosilicate (FIGS. 2A-2B) and after 4 weeks of treatment with the composition (FIGS. 2C-2D).
Figure 2B:
Figure 2C:
Figure 2D:

FIGS. 2A and 2B show the canine prior to treatment with the composition. FIGS. 2C and 2D show the canine after 4 weeks of treatment. These figures demonstrates that the composition containing a mixture of 40% tetraethyl orthosilicate and 60% olive oil was able to successfully treat demodectic mange in a canine Example 9

A composition containing 40% tetraethyl orthosilicate and 60% jojoba oil by volume was prepared by physical mixing. The composition was administered to the forehead of a human patient suffering from basal cell carcinoma twice a day for a period of 2 weeks.

Figure 3A:
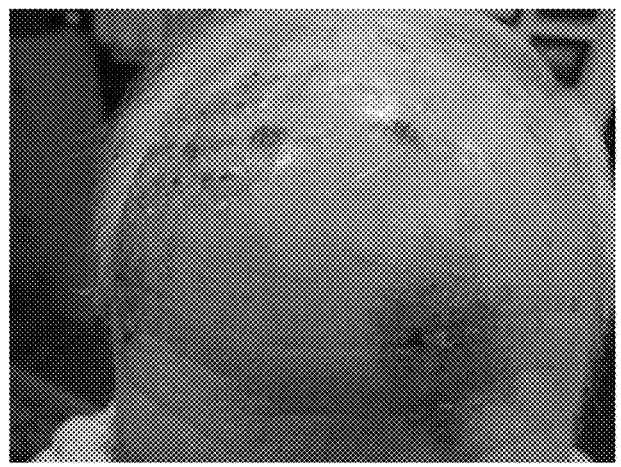
FIGS. 3A-3L depict an individual with basal cell carcinoma before treatment with a composition comprising orthosilicate (FIGS. 3A-3C), 2 days after treatment with the composition (FIGS. 3D-3F), at 1 week of treatment with the composition (FIGS. 3G-3I) and at 2 weeks of treatment with the composition (FIGS. 3J-3L).
Figure 3B:
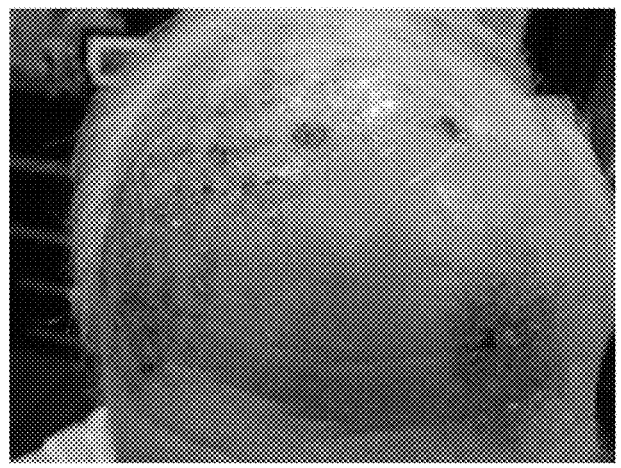
Figure 3C:
Figure 3D:
Figure 3E:
Figure 3F:
Figure 3G:
Figure 3H:
Figure 3I:
Figure 3J:
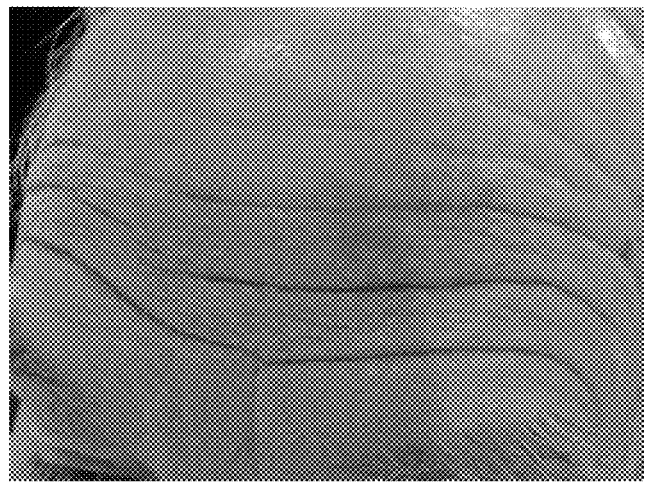
Figure 3K:
Figure 3L:

FIGS. 3A-3C depict the forehead of the patient before treatment. FIGS. 3D-3F show the forehead after 2 days of treatment. FIGS. 3G-3I show the forehead at 1 week of treatment. FIGS. 3J-3L show the forehead at two weeks of treatment. These figures demonstrate that a composition containing a mixture of 40% tetraethyl orthosilicate and 60% jojoba oil is capable of performing tissue regeneration in a patient suffering from basal cell carcinoma.

Example 10

A composition containing 40% tetraethyl orthosilicate and 60% jojoba oil was administered to the scalp of a person lacking hair at the place of administration. The composition was administered once daily for 2 months.

Figure 4:
FIG. 4 depicts an individual with hair regrowth after 2 months of treatment with a composition comprising orthosilicate.

FIG. 4 depicts the scalp of the person after 2 months of treatment. At the place of administration, new hair grew. Surprisingly, the new growth was pigmented and not white like the surrounding, existing hair.

Example 11

A weanling Thoroughbred filly presented with a full skin thickness laceration (approx 3 inches) of the upper right forearm and multiple contusions and abrasions on the leg, as well as on the body and head.

The filly was treated by first undergoing sedation, its injuries lavaged with isotonic fluids, the wound edges trimmed, and then an ointment was applied to the laceration and other injuries. The ointment contained the following components: 100 ml polyethylene glycol 400; 50 g. polyethylene glycol 3540; 5.6 g. salicylic acid; 11 g. benzoic acid; 115 ml tetraethyl orthosilicate; and 10 ml methyl alcohol. The wound was sutured with horizontal mattress sutures. Phenylbutazone and systemic antibiotic was given to the filly.

The filly was confined to a stall for 10 days with daily application of the ointment to the injuries, combined with an oral antibiotic (7 days). The suture was removed at two weeks after several days of turn out.

After the 10-day period, the wound healed uneventfully without complication and the other injuries healed. Hair re-growth was also began quickly.

Example 12

A yearling Thoroughbred filly presented with a Y-shaped full skin thickness laceration of the left chest (at least 6 inches) with a loose flap. The laceration was cleaned and sutured with a simple continuous suture pattern. The filly was also treated with systemic antibiotics. After 5 days, however, wound dehiscence with purulent discharge was evident.

After discovering the wound dehiscence and purulent discharge, the wound was subsequently cleaned and lavaged using an isotonic solution and packed with the ointment from Example 11. The antibiotic treatment was also continued. The combination of the ointment and antibiotic treatment was repeated daily for 2 additional days. Afterwards, loop sutures were placed above and below the wound, loose sutures were removed and the wound was lavaged with the ointment in isotonic solution, covered with the ointment and a bandage laced in place using loops.

After 24 hours, the bandage was removed and a dramatic improvement with seen, evident by a healthy granulating bed of tissue developing. After 3 additional days of treatment with the ointment, a horizontal mattress stay suture over rubber tubing was applied to oppose the tissues, and the wound was treated and re-bandaged with the ointment. The bandage with the ointment was reapplied daily for 2 more days. The wound was subsequently lavaged with additional ointment, trimmed, sutured with horizontal mattress sutures after application of the ointment and rebandaged.

After the foregoing treatment and inspection of the filly, it was evidence that granulation and wound healing was accelerated, and infection was eliminated.

Example 13

A mature Quarter Horse mare presented with a deep wood puncture of the left buttock and a deep laceration involving the left side of the vulva extending between the hind legs to the udder. The wounds were approximately 6 inches deep with a large vulgar flap.

The mare was sedated, the wound was cleaned and the wood was removed. Phenylbutazone and antibiotic given to the mare. After 4 days, the wound was trimmed of necrotic, devitilized tissue and the ointment from Example 11 was applied.

The wound was subsequently cleaned daily and the ointment applied as the only treatment. No infection or discharge was observed and the wounds healed at an accelerated rate from the inside out.

After 3 weeks, the wound was healing nicely with only superficial (less than 1 inch depth) wound remaining. No lameness or restriction of movement was observed, which resulted in a much better than expected progress. A full recovery is expected based on this observation.

Example 14

A yearling Thoroughbred filly presented with a developing mass (suspect sarcoid) on the midline of the face, approximately 1 inch in diameter.

The ointment from Example 11 was applied daily, resulting in a visible "breakdown" and resorption of the mass over approximately a 1-month period. The mass has not reoccurred despite no further treatment after 1 month.

Example 15

Figure 5A:
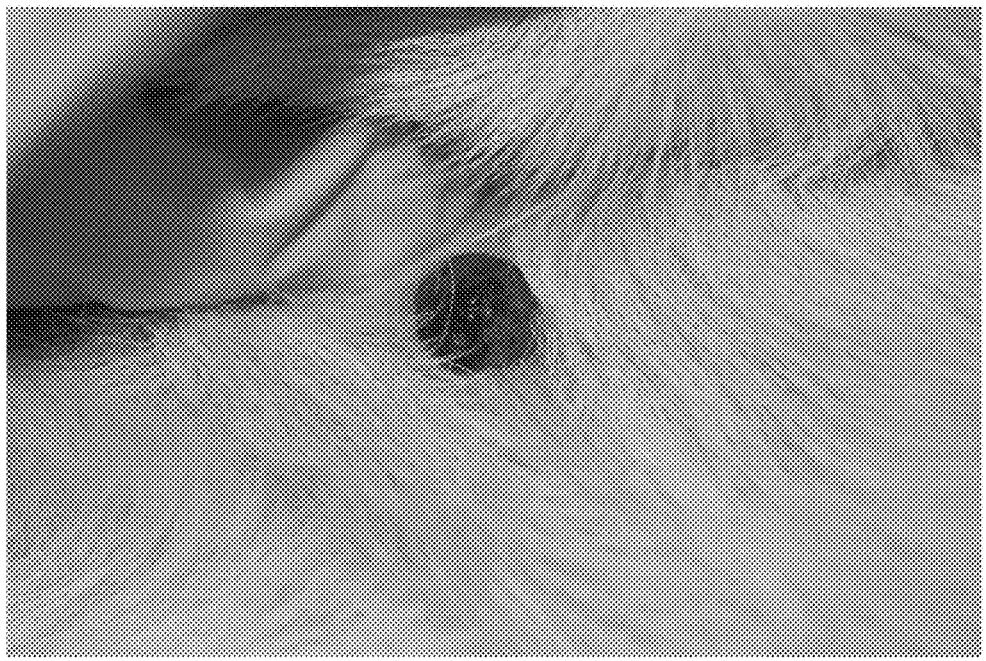
FIGS. 5A-5B depict a Beagle canine with a surface lesion due to melanoma before treatment with a composition comprising orthosilicate (FIG. 5A) and after 7 days of treatment with the composition (FIG. 5B).
Figure 5B:

A Beagle diagnosed with melanoma was administered with a composition containing 40% tetraethyl orthosilicate and 60% jojoba oil by direct application to the surface lesion over a period of 7 days, three times daily, using a cotton swab. FIG. 5A depicts the surface lesion on day 1 of treatment and FIG. 5B depicts the surface lesion on day 7 of the treatment. These figures demonstrate that the composition reduced the melanoma lesion.

Example 16

A composition comprising orthosilicate can be produced in the following manner: melt 10 g. of natural unbleached beeswax, 20 g. of cocoa butter (100% natural) and 20 g. of almond oil together to produce a homogenous mixture with warm, liquid consistency. Then, add 20 g. of tetraethyl orthosilicate to the mixture and cool the mixture with occasional stirring until a cream forms. Greater stirring will yield a lighter cream. The cream can be aliquoted into containers.

Example 17

A composition comprising orthosilicate can be produced in the following manner: dissolve 3 liters of tetraethyl orthosilicate in 2 liters of absolute methanol. Then, add 1.12 kg. of salicylic acid and 2.2 kg. of benzoic acid to the suspension and heat the mixture to 140° F. with stirring until more than 50% of the acids dissolve. At this point, add 20 liters of polyethyleneoxide (400 MW) and continue stirring at the same temperature of 140° F. until a complete solution occurs. Then, while maintaining the temperature of 140° F., add 10 kg. of polyethylene oxide (3500-3700 MW) to the solution and stir until a clear solution develops Aliquot the solution, which should be warm, into containers and allow the solution to cool to produce a gel formation. The gel can be used to treat different diseases and conditions, such as an open wound, including a puncture wound.

Example 18

A cream composition comprising orthosilicate was produced in the following manner: 40 grams of CRODAFOS™ CES and 60 grams of myristyl myristate were mixed well at a temperature of about 75° C. to obtain Part A. The following ingredients at the specific amounts were mixed well: 7 grams of glycerine, 50 grams of caprylyl carbonate, 10.5 grams of aloe vera (10x), 30 grams of dihydroxypropane, 5 grams of glyceryl oleate, 632 grams of 75° C. hot water, 2.5 grams of phenoxyethanol and ethylhexylglycerin, and 13 grams of arginine to adjust pH to pH 8 to obtain Part B. Part A was added to Part B and mixed well, followed by a check of the pH. Subsequently, 125 grams of tetraethyl orthosilicate was added to the mixture of Part A and Part B and mixed well to obtain the cream. Then Q/S with water.

Example 19

The cream produced in Example 18 can be used in treating human scar, melanoma, or basal cell carcinoma. For example, the cream of Example 18 can be applied to a scar, twice daily, for two weeks or more.

Example 20

Figure 6A:
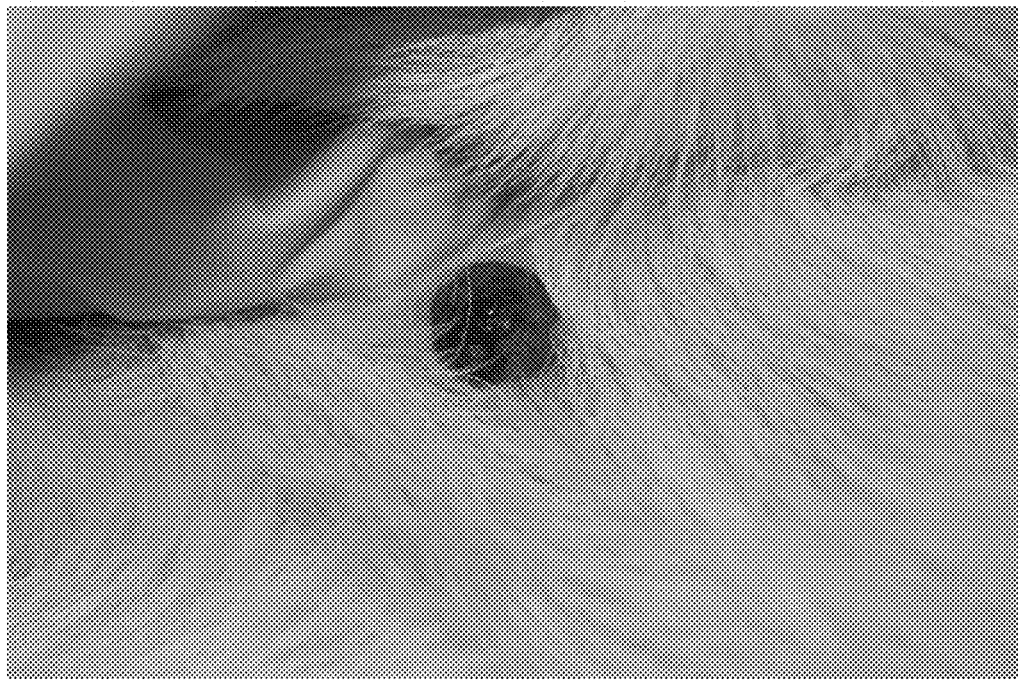
FIGS. 6A-6B depict a canine with a surface lesion due to melanoma before treatment with a composition comprising orthosilicate (FIG. 6A) and after 6 days of treatment with the composition (FIG. 6B).
Figure 6B:

A canine diagnosed with melanoma was administered with the cream of Example 18 by direct application to the surface lesion over a period of 6 days, two or three times daily, using a cotton swab. FIG. 6A depicts the surface lesion prior to treatment and FIG. 6B depicts the surface lesion on day 6 after the treatment. These figures demonstrate that the cream reduced the melanoma lesion.

Example 21

Figure 7A:
FIGS. 7A-7B depict a horse with a surface lesion on the tail due to melanoma before treatment with a composition comprising orthosilicate (FIG. 7A) and after two treatments with the composition within 48 hours (FIG. 7B).
Figure 7B:

A horse diagnosed with melanoma on its tail was administered two treatments of the cream of Example 18 over a period of 48 hours. FIG. 7A depicts the surface lesion on the tail prior to treatment and FIG. 7B depicts the surface lesion after two treatments within 48 hours. As shown in FIG. 7B, the lesions started sloughing off within 48 hours.

Example 22

Figure 8A:
FIGS. 8A-8B depict a wound in a horse before treatment with a composition comprising orthosilicate (FIG. 8A) and after 48 hours of treatment with the composition and before suture (FIG. 8B).
Figure 8B:

The cream of Example 18 was administered to an open wound in a horse over a period of 48 hours. FIG. 8A depicts the wound after initial treatment with standard therapy and FIG. 8B depicts the wound after 48 hours of treatment with the cream of Example 18 and before suture.

Example 23

The cream of Example 18 was applied daily for 5 days to an adult Australian Shepherd presented with an infected bite wound approximately 1"×1½" with purulent discharge. FIG. 9A depicts the original bite site and FIG. 9B depicts the wound after 5 days of treatment with the cream of Example 18. The treatment resulted in complete healing without any scar.

Example 24

Figure 10A:
FIGS. 10A-10B depict a deep laceration just above the coronary band of the foot in an adult Thoroughbred horse before treatment with a composition comprising orthosilicate (FIG. 10A) and after 3 weeks of treatment with the composition (FIG. 10B).
Figure 10B:

An adult Thoroughbred horse was presented with a deep laceration just above the coronary band of the foot. This was a very difficult area to heal due to contamination and movement of the tissues. The wound was cleaned daily with water and bandaged with the cream of Example 18 for 3 weeks. FIG. 10A depicts the wound before treatment and FIG. 10B depicts the wound after 3 weeks of treatment with the cream of Example 18. The wound healed uneventfully without scarring or lameness after the treatment.

Example 25

Figure 11A:
FIGS. 11A-11B depict an infection in the left hind foot of a heifer before treatment with a composition comprising orthosilicate (FIG. 11A) and after 3 weeks of treatment with the composition (FIG. 11B).
Figure 11B:

A two-year old female American Shorthorn heifer was presented with lameness and a proliferative mass (3" in diameter) with associated swelling and large dense scab between the digits of the left hind foot diagnosed as chronic Foot Rot. The heifer was treated with a 7-day course of oral antibiotic with some improvement in swelling and lameness but the scabbing and proliferative area remained. After 4 months lameness reoccurred and the area again became inflamed. The heifer was treated with Nuflor (an injectable antibiotic) for 7 days with reduction of mass size by approximately ⅓ and reduced lameness. A surgical consultation determined that the area needed to be surgically excised under general anesthesia. Due to late term pregnancy, surgery was postponed until after delivery. While waiting for surgery, the cream of Example 18 was applied once daily by massaging the cream into the area between the digits. Within the first week, the lesion began to reduce in size and the scabbing loosened allowing the cream to be worked under it. After 2 weeks, the scab came off and the lesion was reduced by at least 75% with no associated lameness. At week 3, the lesion was barely noticeable with no lameness. No surgery or further antibiotic therapy was anticipated. FIG. 11A depicts the infection in the left hind foot before treatment and FIG. 11B depicts the infected area after 3 weeks of treatment with the cream of Example 18.

This successful treatment was significant because it resulted in significant reduction in cost and risk by eliminating the need for surgery and general anesthesia.

Example 26

A yearling Thoroughbred filly presented with a developing mass (suspect sarcoid) on the midline of the face approximately 1 inch in diameter. The filly was treated by daily application of the cream of Example 18. The treatment resulted in a visible "breakdown" and resorption of the mass over approximately one-month period. After the one-month treatment, no further treatment was required as the mass did not reoccur.

Example 27

A weanling Thoroughbred filly presented with a full skin thickness laceration (approx 3 inches) of the upper right forearm and multiple contusions and abrasions on the leg, as well as on the body and head.

The filly was treated by first undergoing sedation, its injuries lavaged with isotonic fluids, the wound edges trimmed, and then the cream of Example 18 was applied to the laceration and other injuries. The wound was sutured with horizontal mattress sutures. Phenylbutazone and systemic antibiotic were given to the filly.

The filly was confined to a stall for 10 days with daily application of the cream of Example 18 to the injuries, combined with an oral antibiotic (7 days). The suture was removed at two weeks after several days of turn out.

After the 10-day period, the wound healed uneventfully without complication and the other injuries healed. Hair re-growth also began quickly.

Example 28

A mature Quarter Horse mare presented with a deep wood puncture of the left buttock and a deep laceration involving the left side of the vulva extending between the hind legs to the udder. The wounds were approximately 6 inches deep with a large vulgar flap.

The mare was sedated, the wound was cleaned and the wood was removed. Phenylbutazone and antibiotic given to the mare. After 4 days, the wound was trimmed of necrotic, devitilized tissue and the cream of Example 18 was applied.

The wound was subsequently cleaned daily and the cream of Example 18 applied as the only treatment. No infection or exudate was observed and the wounds healed at an accelerated rate from the inside out.

After 10 days, the wound was healing nicely with only superficial (less than 1 inch depth) wound remaining. No lameness or restriction of movement was observed, which resulted in a much better than expected progress. A full recovery was expected based on this observation.

FIG. 12A depicts the wound before the treatment, FIG. 12B depicts the wound after 10 days of treatment, and FIG. 12C depicts the wound after 21 days of treatment with the cream of Example 18.

What is claimed is:
1. A composition consisting essentially of tetraethyl orthosilicate and at least one oil selected from the group consisting of jojoba oil, almond oil, cocoa butter, bees wax, and sweet almond oil, wherein the tetraethyl orthosilicate is present in a concentration from 25% to 40% by total weight of the composition, and wherein the composition is presented as a cream or an ointment.

2. The composition according to claim 1, wherein the oil is jojoba oil.

3. The composition according to claim 1, wherein the oil is a combination of cocoa butter, bees wax, and sweet almond oil.

4. The composition of claim 1, further comprising a component selected from the group consisting of an excipient, stabilizer, moisturizer, thickening agent, emulsifier, emollient, lubricant, surfactant, deodorizing agent, viscosity controlling agent, solvent, softening agent, alkalizing agent, vitamin, opacifying agent, solubilizer, plant extract, water, chelating agent, humectant, thickener, cryoprotectant, biocide, nebulizer, anti-oxidant, lipid, peptide, protein, amino acid, anti-aging agent, anti-wrinkle agent, fragrance, essential oil, and preservative.

5. A composition consisting of tetraethyl orthosilicate; at least one oil selected from the group consisting of jojoba oil, almond oil, aloe vera oil, olive oil, cocoa butter, bees wax, and sweet almond oil; and optionally one or more components selected from the group consisting of an excipient, stabilizer, moisturizer, thickening agent, emulsifier, emollient, lubricant, surfactant, deodorizing agent, viscosity controlling agent, solvent, softening agent, alkalizing agent, vitamin, opacifying agent, solubilizer, plant extract, water, chelating agent, humectant, thickener, cryoprotectant, biocide, nebulizer, anti-oxidant, lipid, peptide, protein, amino acid, anti-aging agent, anti-wrinkle agent, fragrance, essential oil, and preservative;

wherein the tetraethyl orthosilicate is present in a concentration from 25% to 40% by total weight of the composition, and wherein the composition is presented as a cream or an ointment.

6. The composition according to claim 5, wherein the at least one oil is jojoba oil.

7. The composition according to claim 5, wherein the at least one oil is selected from the group consisting of aloe vera oil, cocoa butter, bees wax, and sweet almond oil.

8. The composition according to claim 5, wherein total oil content is 10% to 90% by total weight of the composition.

9. The composition according to claim 5, wherein total oil content is 50% to 75% by total weight of the composition.

10. The composition according to claim 1, wherein total oil content is 10% to 90% by total weight of the composition.

11. The composition according to claim 1, wherein total oil content is 50% to 75% by total weight of the composition.

* * * * *